United States Patent
Nouguerede et al.

(10) Patent No.: US 9,180,317 B2
(45) Date of Patent: Nov. 10, 2015

(54) COSMETIC COMPOSITION FOR NAILS AND THE USE OF AN ISOSORBIDE DERIVATIVE

(75) Inventors: Olivier Nouguerede, Hanches (FR); Francisco Martinez, Chartres (FR)

(73) Assignee: FIABILA, Maintenon (FR)

( * ) Notice: Subject to any disclaimer, the term of this patent is extended or adjusted under 35 U.S.C. 154(b) by 583 days.

(21) Appl. No.: 12/847,201

(22) Filed: Jul. 30, 2010

(65) Prior Publication Data

US 2012/0003166 A1    Jan. 5, 2012

(30) Foreign Application Priority Data

Jul. 1, 2010 (FR) ...................................... 10 55283

(51) Int. Cl.
- *A61Q 3/02* (2006.01)
- *A61K 8/60* (2006.01)
- *A61K 8/73* (2006.01)
- *A61K 8/85* (2006.01)

(52) U.S. Cl.
CPC ... *A61Q 3/02* (2013.01); *A61K 8/60* (2013.01); *A61K 8/731* (2013.01); *A61K 8/85* (2013.01); *A61K 8/604* (2013.01)

(58) Field of Classification Search
None
See application file for complete search history.

(56) References Cited

U.S. PATENT DOCUMENTS

| 4,073,968 | A | * | 2/1978 | Miyamoto et al. | 427/511 |
| 5,227,155 | A | | 7/1993 | Castrogiovanni et al. | |
| 5,646,200 | A | * | 7/1997 | Duncan | 523/160 |
| 2003/0144158 | A1 | * | 7/2003 | Petelot | 508/318 |
| 2010/0158835 | A1 | | 6/2010 | Bandres et al. | |

FOREIGN PATENT DOCUMENTS

| EP | 2174641 A1 | 4/2010 |
| FR | 2895905 A1 | 7/2007 |
| WO | 99/45060 A1 | 9/1999 |
| WO | 2006/103338 A1 | 10/2006 |

OTHER PUBLICATIONS

French Search Report, dated Mar. 23, 2011, in FA 737686/FR 1055283.

* cited by examiner

*Primary Examiner* — Bethany Barham
*Assistant Examiner* — Barbara Frazier
(74) *Attorney, Agent, or Firm* — Young & Thompson

(57) ABSTRACT

A cosmetic composition for nails containing a plasticizer of natural origin, a derivative of sorbitol, and the use of isosorbide diester as a plasticizer in cosmetic compositions for nails.

14 Claims, No Drawings

COSMETIC COMPOSITION FOR NAILS AND THE USE OF AN ISOSORBIDE DERIVATIVE

FIELD OF THE INVENTION

This invention relates to the field of compositions for nails, in particular the cosmetic compositions for nails, such as nail polishes.

BACKGROUND OF THE INVENTION

In a conventional manner, nail polishes contain the following as primary components: organic or aqueous solvents, at least one film-forming compound and a plasticizer, pigments and/or coloring compounds. For several years, efforts have been made to formulate compositions for nails without either phthalates or condensation products of acetaldehyde, compounds that have proven hazardous to health. It is therefore desired to develop new plasticizers that are less toxic and/or less volatile.

Furthermore, the current tendency, in all of the sectors, and in particular in the field of cosmetics, is increasingly to turn to so-called natural products, in particular products derived from plant substances.

The formulator, however, is confronted with many difficulties and constraints. Actually, each change in component or each modification of the concentration of a component has an effect on the properties that are desired for the polishes, such as adhesion, gloss, and hardness, but also flexibility.

For example, for several years, acetyl tributyl citrate (ATC) (cited in particular in U.S. Pat. No. 5,227,155) almost exclusively replaced the phthalates that were initially used as plasticizers. It was observed, however, that ATC imparts lower gloss to the polish than the phthalates.

Furthermore, it was noted that certain so-called natural plasticizers promote either an uptake of water of the polish, i.e., they have the drawback of leading to, after the polish dries on the nail, an absorption of water (for example when the individual bathes, washes or has her hands in water for household activities . . . ) or a degradation by migration in the water of the hydrophilic components of the polish; this is the case of, for example, carbonate-based plasticizers, such as glycerol carbonate (WO2007/080172). This water absorption that causes a swelling of the polish, or this degradation, leads to a reduction of its strength and a loss of adhesion. These consequences are very detrimental to keeping the polish on the nail.

There have been similar findings with nail polishes that contain ATC in areas with high hygrometry. These polishes exhibited adhesion defects, which have turned out to be caused by the absorption of ambient moisture.

SUMMARY OF THE INVENTION

One object of this invention is therefore to propose a cosmetic composition for nails that overcomes the drawbacks above by meeting the required criteria for adhesion and gloss and exhibiting a good hardness/flexibility compromise.

The component that plays a major role in obtaining these properties being the plasticizer, another object of the invention is to propose a plasticizer of natural origin, not causing swelling, i.e., with reduced water absorption, so as to impart low water uptake after drying to the polish applied to the nail.

These objects are achieved by the cosmetic composition for nails according to this invention, characterized in that it contains a plasticizer of natural origin, derived from sorbitol. The applicant discovered in particular, in a surprising manner, that isosorbide diesters could satisfy this plasticizer function within polish compositions, in particular by imparting to these polishes properties that are superior to the compositions that contain plasticizers of the prior art.

Isosorbide is a product that is obtained by dehydration of a derivative of glucose: sorbitol, which in particular can be extracted from service berries or grains. Diester is advantageously produced by reaction between a fatty acid of plant origin and isosorbide.

Thus, in formula (I) below:

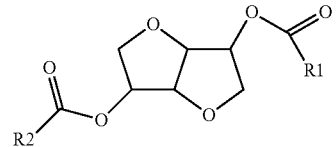

the radicals R1 and R2 are linear or branched $C_2$ to $C_{22}$ alkyl radicals that are identical or different.

Advantageously, R1 and R2 are identical and are preferably linear or branched $C_6$ to $C_{12}$ alkyl radicals.

According to the invention, the plasticizer can be selected from among the following compounds: isosorbide dihexanoate, isosorbide diheptanoate, isosorbide dioctanoate, isosorbide didecanoate, isosorbide didodecanoate, isosorbide di(2-ethylhexanoate) or a mixture of the latter.

These plasticizers respond to the technical problem mentioned above by making it possible to develop cosmetic compositions for nails that exhibit a good hardness/flexibility compromise with a good compatibility with the other components of the formula. Correct adhesion as well as very low water absorption of polishes formulated with such plasticizers are also noted.

These isosorbide diesters are also products that are obtained from natural substances and are biodegradable products. Actually, isosorbide is obtained by dehydration of sorbitol, itself obtained here from grains. The fatty acids that are used for the production of diester are obtained from vegetable oils.

The plasticizer is advantageously present in the cosmetic composition for nails in a concentration of between 0.1 and 30% by weight, preferably 3 to 20% by weight, and even more preferably between 5 and 15% by weight.

This cosmetic composition can be used as a base for polish (base coat), as a make-up polish for the nails, as a finishing composition (top coat) for the nails, or as a composition for cosmetic care of the nails. This composition can be applied to the human nail or to fake nails.

This composition can also contain a primary film-forming polymer that is derived from cellulose, such as nitrocellulose, cellulose acetate, cellulose acetobutyrate, cellulose acetopropionate, or a mixture of the latter, one or more secondary film-forming polymers such as polyester resins, acrylic alkyds, epoxy-tosylamides, polyurethanes, poly-amides, . . . , mineral or organic thickening agents, such as silicas, modified clays, coloring materials such as pigments or mother-of-pearl, additives such as anti-UV agents, wetting agents, spreading and/or sliding agents, hydrating agents, active ingredients (Vitamins B5, E, C, amino acids, oils, . . . ) and/or perfumes.

This invention also relates to the use of the isosorbide derivative, and more specifically the isosorbide diester as a plasticizer in cosmetic compositions for the nails.

DETAILED DESCRIPTION OF THE INVENTION

This invention will be better understood using the following description of examples that are mentioned by way of illustration.

EXAMPLES

Different plasticizers have been tested:

Example 1

Isosorbide dioctanoate, product marketed by the ROQUETTE Company under the name Polysorb ID37.

Example 2

For Comparison

Acetyl tributyl citrate (as used in the prior art—see U.S. Pat. No. 5,227,155)

Example 3

For Comparison

Diethylene glycol dibenzoate

Example 4

For Comparison

Glyceryl tribenzoate

Example 5

For Comparison

Glycerol carbonate (as cited in the application WO 2007/080172)

The general formula that is used for comparing the different plasticizers was as follows:

TABLE 1

| Component | % by Weight |
|---|---|
| Ethyl acetate | 20.77 |
| Butyl acetate | 40.50 |
| Nitrocellulose (70% in isopropanol) | 18.00 |
| Plasticizer | 10.00 |
| Polyester resin (trimellitic anhydride/adipic acid/neopentyl glycol) at 70% in butyl acetate | 9.00 |
| Phosphoric acid | 0.03 |
| Bentonite | 1.50 |
| Diacetone alcohol | 0.20 |
| TOTAL | 100.00 |

(The percentages are expressed by total weight of the composition)

This formula has been optimized in terms of performances (see below). The majority of the components come from the plant domain. Nitrocellulose could also be provided at 70% in ethanol, which would make it possible to increase the percentage of raw materials obtained from plants in the final formula.

The tests that are conducted on these different polishes are as follows (the desired values of the different parameters that are measured are noted between parentheses):

Gloss: A polish film of 100 μm is applied on a Leneta plate. It is dried, and then by means of a brilliance meter, the gloss is measured at an angle of 60° (a value of greater than 80° is desired).

Flexibility: A slow embossing is implemented on an aluminum plate that is covered by a moist polish of 300 μm, and the depth of the penetration is measured (ISO1520) (a value of greater than 3.0 is desired, preferably greater than 4.0).

Hardness: Persoz hardness on a glass plate covered by a moist polish of 100 μm (ISO1522) (a minimum value of 180 is necessary, preferably 220).

Immersion in water: A previously dried film is immersed for 24 hours in water at a temperature of 25° C. The variation of mass of the film before and after immersion is measured (the weakest value possible is desired for limiting the swelling that would cause softening and detachment of the polish).

Adhesion: "Cross hatch test" conducted on the glass plate. The grade 0 corresponds to the absence of adhesion loss. The grade 5 corresponds to the total loss of adhesion (a value of between 0 and 1 is necessary).

Dry extract: Between 0.5 g and 1 g of polish is weighted in a cupel. Then, this plate is placed in an oven for 3 hours at 100° C. The cupel is weighed after being run through the oven, and the dry extract of the polish is calculated (the usual values are generally between 30 and 32% by weight of dry extract).

The results that are obtained are assembled in Table 2, which follows.

TABLE 2

|  | Ex. 1 | Ex. 2 (Comp) | Ex. 3 (Comp) | Ex. 4 (Comp) | Ex. 5 (Comp) |
|---|---|---|---|---|---|
| Dry extract (%) | 30.7 | 31.2 | 31.1 | 32.2 | 30.4 |
| Hardness (s) | 248 | 229 | 220 | 246 | 60 |
| Flexibility (mm) | 4.6 | 5.3 | 4.6 | 1.5 | 5.9 |
| Gloss (60°, UB) | 88.5 | 83.5 | 90.3 | 90.3 | 84.4 |
| Adhesion | 0.1 | 0.1 | 2 | 0.1 | 5 |
| Changes in mass after immersion (%) | +2.4 | +4.2 | +2.6 | +2 | −14.4 |

It is noted among the plasticizers that none of the plasticizers of the Examples 2, 3, 4, and 5 for comparison are satisfactory.

Actually, acetyl tributyl citrate (Example 2 for comparison) exhibits a lower gloss and greater water uptake relative to isosorbide dioctanoate.

Example 3 for comparison shows that diethylene glycol dibenzoate exhibits inadequate adhesion.

Glycerol tribenzoate (Example 4 for comparison) exhibits a flexibility that is very inferior to that of other plasticizers and that is very inadequate for use in such a polish composition.

As for glycerol carbonate, it is also to be excluded since it exhibits a very low hardness as well as a lower gloss than the other plasticizers. Its adhesion is also very inadequate with a total loss of adhesion.

In addition, it exhibits a significant degradation after immersion in water, with a significant loss of mass.

Excellent performances of isosorbide dioctanoate relative to other plasticizers under the same operating conditions are therefore noted.

Example 6

In this example, the concentration of plasticizer of the formula of Example 1 is varied. The results of formulas A, B and C are recorded in Table 3 below.

TABLE 3

|  | Formulas | | |
| --- | --- | --- | --- |
|  | A | B | C |
| Ethyl acetate | 20.77 | 20.77 | 20.77 |
| Butyl acetate | 38.5 | 40.5 | 42.5 |
| Nitrocellulose (70% in isopropanol) | 18 | 18 | 18 |
| Isosorbide dioctanoate | 12 | 10 | 8 |
| Polyester resin (TMA/adipic acid/NPG) | 9 | 9 | 9 |
| Phosphoric acid | 0.03 | 0.03 | 0.03 |
| Bentonite | 1.5 | 1.5 | 1.5 |
| Diacetone alcohol | 0.2 | 0.2 | 0.2 |

Only the solvent concentration was modified to take into account the different variations of percentage by weight of plasticizer.

The results of the different tests obtained with these three formulas A, B and C are recorded in Table 4 below.

TABLE 4

|  | Test A | Test B | Test C |
| --- | --- | --- | --- |
| Dry extract (%) | 32.5 | 30.7 | 28.6 |
| Hardness (s) | 189 | 248 | 309 |
| Flexibility (mm) | 5.7 | 4.6 | 3.1 |
| Gloss (60°, UB) | 88.6 | 88.5 | 87.5 |
| Adhesion | 0-1 | 0-1 | 0-1 |

It is therefore seen that in the formulas described in Table 1, the optimal quantity of isosorbide dioctanoate is on the order of 10% by weight. The greater concentrations lead to a lower hardness and lower concentrations lead to less flexibility.

However, this optimal concentration can vary based on the nature and the concentration of the other raw materials that are present in the nail polish.

The invention has been described according to a particular embodiment; it is obvious that it is in no way limited thereto and that it comprises all of the described technical equivalents that are part of the scope of the claims.

The composition of Example B comprises 84% of raw material of natural origin by using solvents of plant origin. This level could easily rise to 92% if a nitrocellulose diluted in the ethanol of plant origin was used.

The invention claimed is:

1. A nail polish composition, comprising:
   at least one solvent;
   nitrocellulose;
   one or more polyester resin(s) comprising trimellitic anhydride/adipic acid/neopentyl glycol copolymer;
   a mineral thickening agent comprising bentonite; and
   5% to 15% by weight of a plasticizer comprising an isosorbide diester of formula (I):

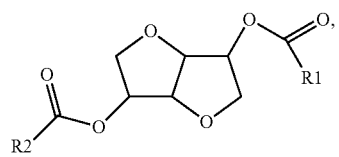

R1 and R2 each independently being a linear or branched $C_6$ to $C_{12}$ alkyl radical,
   wherein the composition has a flexibility measured by ISO1520 of greater than 3.0 and a hardness measured by ISO1522 of at least 180, and a dried film of the composition has a gloss value measured at an angle of 60° of greater than 80°.

2. The composition according to claim 1, wherein R1 and R2 are identical.

3. The composition according to claim 1, wherein the plasticizer is a compound selected from the group consisting of: isosorbide dihexanoate, isosorbide diheptanoate, isosorbide dioctanoate, isosorbide didecanoate, isosorbide didodecanoate, isosorbide di(2-ethylhexanoate) and mixtures thereof.

4. The composition according to claim 1, wherein the plasticizer is present in a concentration of between 8% to 12% by weight.

5. The composition according to claim 1, wherein the composition is a base for nail polish, a make-up nail polish, a finishing nail polish, or a cosmetic care nail polish.

6. The composition according to claim 1, further comprising a compound selected from the group consisting of organic thickening agents, pigments, mother-of-pearl, anti-UV agents, wetting agents, spreading and/or sliding agents, hydrating agents, vitamins, perfumes, and mixtures thereof.

7. The composition according to claim 1, wherein the nitrocellulose is in ethanol or isopropanol.

8. The composition according to claim 1, wherein the solvent comprises a mixture of acetate solvents.

9. The composition according to claim 8, wherein the solvent comprises ethyl acetate and butyl acetate.

10. The composition according to claim 1, comprising 8% to 12% by weight of the plasticizer isosorbide dioctanoate.

11. The composition according to claim 10, comprising 1.5% by weight of bentonite.

12. The composition according to claim 1, wherein the one or more polyester resin consists of trimellitic anhydride/adipic acid/neopentyl glycol copolymer.

13. The nail polish composition according to claim 1, comprising:
   12.6% by weight of nitrocellulose;
   6.3% by weight of polyester resin;
   1.5% by weight of bentonite;
   8% to 12% by weight of isosorbide dioctanoate; and
   solvent comprising at least one of ethyl acetate and butyl acetate.

14. The nail polish composition according to claim 1, wherein the composition has a flexibility measured by ISO1520 of greater than 4.0 and a hardness measured by ISO1522 of at least 220.

* * * * *